(12) United States Patent
Jensen et al.

(10) Patent No.: US 12,121,688 B2
(45) Date of Patent: Oct. 22, 2024

(54) MEDICAL DEVICE WITH ACTUATION MECHANISM

(71) Applicant: Novo Nordisk A/S, Bagsvaerd (DK)

(72) Inventors: Brian Jensen, Broenshoej (DK); Morten Revsgaard Frederiksen, Copenhagen K (DK); Brian Mouridsen, Fredensborg (DK); Jacob Pyung Hwa Jepsen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 618 days.

(21) Appl. No.: 17/426,848

(22) PCT Filed: Jan. 31, 2020

(86) PCT No.: PCT/EP2020/052521
§ 371 (c)(1),
(2) Date: Jul. 29, 2021

(87) PCT Pub. No.: WO2020/157324
PCT Pub. Date: Aug. 6, 2020

(65) Prior Publication Data
US 2022/0105330 A1   Apr. 7, 2022

Related U.S. Application Data

(60) Provisional application No. 62/799,882, filed on Feb. 1, 2019.

(30) Foreign Application Priority Data

Jun. 7, 2019 (EP) .................................... 19179205
Jun. 7, 2019 (EP) .................................... 19179206

(51) Int. Cl.
*A61M 37/00* (2006.01)
*A61M 31/00* (2006.01)

(52) U.S. Cl.
CPC ...... *A61M 37/0069* (2013.01); *A61M 31/002* (2013.01); *A61M 2210/1053* (2013.01);
(Continued)

(58) Field of Classification Search
CPC .................. A61M 5/2033; A61M 5/30; A61M 2005/202; A61M 2202/0007;
(Continued)

(56) References Cited

U.S. PATENT DOCUMENTS 4,425,117 A   1/1984   Hugemann et al.
7,717,862 B2  5/2010   Stoltz
(Continued)

FOREIGN PATENT DOCUMENTS

CN   101098729 A   1/2008
CN   103025319 A   4/2013
(Continued)

*Primary Examiner* — Jason E Flick
(74) *Attorney, Agent, or Firm* — Wesley Nicolas (57) ABSTRACT

A medical delivery device suitable for insertion into a lumen of a patient, the medical device (100, 200) comprising a capsule (110, 120, 210, 220) sized to be inserted into the lumen, the capsule comprising a base member, and an actuation mechanism comprising an actuation member (150, 250, 350) configured for movement relative to the base member along an axis, and an energy source (140, 240, 340) associated with the actuation member for powering the actuation member to move relative to the base member along the axis. The base member and the actuation member define a latch assembly comprising: a) a dissolvable firing member (160, 260, 360), the dissolvable firing member being at least partially dissolvable when subjected to a biological fluid, b) a retainer portion (113, 213, 313) comprised by one of the base member and the actuation member, and c) a movable latch (152, 252, 352) configured for lateral movement relative to the axis, the movable latch defining a first surface with a blocking portion (153, 253, 353), and a (Continued)

second surface (152a, 252a, 352a) configured for interacting with the dissolvable firing member (160, 260, 360). In a pre-firing configuration, the blocking portion (153, 253, 353) of the movable latch engages the retainer portion (113, 213, 313) in a latching engagement, and the second surface (152a, 252a, 352a) of the movable latch interacts with the dissolvable firing member to restrict lateral movement of the movable latch thereby preventing release of the latching engagement. In a firing configuration where the dissolvable firing member (160, 260) has become at least partially dissolved, the movable latch is allowed to move laterally thereby releasing the latching engagement.

40 Claims, 3 Drawing Sheets

(52) U.S. Cl.
CPC .............. *A61M 2210/106* (2013.01); *A61M 2210/1064* (2013.01)

(58) Field of Classification Search
CPC ...... A61M 2202/30; A61M 2210/1042; A61M 31/002; A61M 2005/206; A61M 5/3202; A61M 31/00; A61M 5/286; A61M 37/0069; A61M 2210/1053; A61M 2210/106; A61M 2210/1064; A61K 9/0024

See application file for complete search history.

(56) References Cited

U.S. PATENT DOCUMENTS

| | | | |
|---|---|---|---|
| 8,969,293 | B2 | 3/2015 | Imran |
| 9,629,810 | B2 | 4/2017 | Schwarz |
| 10,166,486 | B2 | 1/2019 | Erhart et al. |
| 10,428,732 | B2 | 10/2019 | Lynn |
| 10,512,729 | B2 | 12/2019 | Grimoldby et al. |
| 2001/0007059 | A1 | 7/2001 | Mirzaee |
| 2005/0267414 | A1 | 12/2005 | Abraham-Fuchs et al. |
| 2008/0294143 | A1 | 11/2008 | Tanaka et al. |
| 2009/0043278 | A1 | 2/2009 | Tanaka et al. |
| 2009/0270797 | A1 | 10/2009 | Aubert et al. |
| 2009/0306633 | A1 | 12/2009 | Trovato et al. |
| 2010/0121307 | A1 | 5/2010 | Lockard et al. |
| 2011/0160129 | A1 | 6/2011 | Imran |
| 2011/0244238 | A1 | 10/2011 | Panz et al. |
| 2012/0095290 | A1 | 4/2012 | Kawano |
| 2015/0064241 | A1 | 3/2015 | Conrad |
| 2016/0279343 | A1 | 9/2016 | MacDonald et al. |
| 2017/0156909 | A1 | 6/2017 | Brister et al. |
| 2017/0174758 | A1 | 6/2017 | Imran |
| 2017/0252016 | A1 | 9/2017 | Wrigglesworth et al. |
| 2017/0354807 | A1 | 12/2017 | Lozevski |
| 2018/0008771 | A1 | 1/2018 | Mran et al. |
| 2018/0070857 | A1* | 3/2018 | Jones ................... A61B 5/065 |
| 2019/0274663 | A1 | 9/2019 | Rees et al. |
| 2020/0009371 | A1 | 1/2020 | Langer et al. |
| 2020/0038000 | A1 | 2/2020 | Wang |
| 2020/0129441 | A1 | 4/2020 | Abramson et al. |
| 2020/0330269 | A1 | 10/2020 | Bley et al. |

FOREIGN PATENT DOCUMENTS

| | | |
|---|---|---|
| CN | 104069585 A | 10/2014 |
| CN | 105539808 A | 5/2016 |
| CN | 105556096 A | 5/2016 |
| CN | 105828854 A | 8/2016 |
| CN | 105999526 A | 10/2016 |
| CN | 106584474 A | 4/2017 |
| CN | 106999780 A | 8/2017 |
| CN | 107106798 A | 8/2017 |
| CN | 206755400 U | 12/2017 |
| CN | 108136122 A | 6/2018 |
| CN | 108836237 A | 11/2018 |
| CN | 109640899 A | 4/2019 |
| JP | H09290075 A | 11/1997 |
| JP | 2013515576 A | 5/2013 |
| WO | 94/07562 A1 | 4/1994 |
| WO | 200145789 A2 | 6/2001 |
| WO | 2005097238 A2 | 10/2005 |
| WO | 2006126653 A1 | 11/2006 |
| WO | 2007069697 A1 | 6/2007 |
| WO | 2010137705 A1 | 12/2010 |
| WO | 2011079302 A2 | 6/2011 |
| WO | 200002229 A2 | 9/2011 |
| WO | 2014159604 A1 | 10/2014 |
| WO | 2015035111 A1 | 3/2015 |
| WO | 2017156347 A1 | 9/2017 |
| WO | 18060673 A1 | 4/2018 |
| WO | 2018213579 A1 | 11/2018 |
| WO | 2018213593 A1 | 11/2018 |
| WO | 2018213600 A1 | 11/2018 |
| WO | 2019222572 A1 | 11/2019 |
| WO | 2020157324 A1 | 8/2020 |
| WO | 2020160399 A1 | 8/2020 |
| WO | 2020245448 A1 | 12/2020 |
| WO | 2021013907 A1 | 1/2021 |

\* cited by examiner

MEDICAL DEVICE WITH ACTUATION MECHANISM

CROSS-REFERENCE TO RELATED APPLICATIONS

This application is a 35 U.S.C. § 371 National Stage application of International Application PCT/EP2020/052521 (published as WO 2020/157324), filed Jan. 31, 2020, which claims priority to European Patent Applications 19179205.0, filed Jun. 7, 2019, and 19179206.8, filed Jun. 7, 2019, this application further claims priority under 35 U.S.C. § 119 of U.S. Provisional Application 62/799,882, filed Feb. 1, 2019; the contents of which are incorporated herein by reference.

The present invention relates to medical devices, including systems for drug delivery, adapted for being inserted into a lumen of a patient and capable of being activated by means of a fluid, such as a biological fluid.

BACKGROUND OF THE INVENTION

In the disclosure of the present invention reference is mostly made to the treatment of diabetes by delivery of insulin, however, this is only an exemplary use of the present invention.

May people suffer from diseases, such as diabetes, which requires them to receive injections of drugs on a regular and often daily basis. To treat their disease these people are required to perform different tasks which may be considered complicated and may be experienced as uncomfortable. Furthermore, it requires them to bring injection devices, needles and drugs with them when they leave home. It would therefore be considered a significant improvement of the treatment of such diseases if treatment could be based on oral intake of tablets or capsules.

However, such solutions are very difficult to realise, since protein-based drugs will be degraded and digested rather than absorbed when ingested.

To provide a working solution for delivering insulin into the bloodstream through oral intake, the drug has to be delivered firstly into a lumen of the gastrointestinal tract and further into the wall of the gastrointestinal tract (lumen wall). This presents several challenges among which are: (1) The drug has to be protected from degradation or digestion by the acid in the stomach. (2) The drug has to be released while being in the stomach, or in the lower gastrointestinal tract, i.e. after the stomach, which limits the window of opportunity for drug release. (3) The drug has to be delivered at the lumen wall to limit the time exposed to the degrading environment of the fluids in the stomach and in the lower gastrointestinal tract. If not released at the wall, the drug may be degraded during its travel from point of release to the wall or may pass through the lower gastrointestinal tract without being absorbed, unless being protected against the decomposing fluids.

Prior art references relating to oral dosing of active agents and addressing one or more of the above challenges include WO 2018/213600 A1 and WO 2017/156347 A1.

Ingestible capsules have been proposed wherein an actuation mechanism relies on exposure for a predefined time to a biological fluid for a dissolvable retaining member to become sufficiently dissolved for firing the actuation mechanism. Such solutions generally have relied upon a dissolvable retaining member with a precise geometry, tolerances equal to moulded plastic parts, high strength and a short dissolving time.

For this kind of actuation mechanism, typical constraints and requirements for obtaining a well-functioning mechanism include the following:
  the ability to maintain an actuation member against the load of a drive spring for a prolonged time,
  the actuation member shall be kept in place during dissolving of the dissolvable retaining member in order to maintain the desired acceleration when fired, and
  the dissolvable retaining member needs to be totally dissolved to avoid undissolved pieces that could block the actuation mechanism.

Having regard to the above, it is an object of the present invention to provide a medical device for insertion into a lumen of a patient, and which to a high degree effectively and reliably allows firing of an actuation mechanism in a controlled and predictable manner by influence of a biological fluid.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a medical device suitable for insertion into a lumen of a patient, the lumen having a lumen wall, is provided. The medical device comprises a capsule sized to be inserted into the lumen, the capsule comprising a base member, and an actuation mechanism comprising an actuation member configured for movement relative to the base member along an axis, and an energy source associated with the actuation member for powering the actuation member to move relative to the base member along the axis. The base member and the actuation member define a latch assembly comprising at least one pair of a latch and a retainer portion structured to maintain the actuation member in a pre-firing configuration. For each pair of latch and retainer portion the medical device defines: a) a dissolvable firing member, the dissolvable firing member being at least partially dissolvable when subjected to a biological fluid, b) a retainer portion comprised by one of the base member and the actuation member, and c) a movable latch configured for lateral movement relative to the axis, the movable latch defining a first surface with a blocking portion, and a second surface configured for interacting with the dissolvable firing member. In the pre-firing configuration, the blocking portion of the movable latch engages the retainer portion in a latching engagement, and the second surface of the movable latch interacts with the dissolvable firing member to restrict lateral movement of the movable latch thereby preventing release of the latching engagement. In a firing configuration where the dissolvable firing member has become at least partially dissolved, the movable latch is allowed to move laterally thereby releasing the latching engagement between the blocking portion of the movable latch and the retainer portion to allow the energy source to fire the actuation member.

By this arrangement, instead of having a dissolvable member that carries the whole power or load of the energy source, primarily exerted to shear forces, the dissolvable part is designed to simply block a mechanical actuation system in a manner where the dissolvable part is primarily exerted to compression forces. The mechanical actuation system may be designed to rely on parts made from a suitable high-strength material, such as plastic, or metal and do not leave any undissolved pieces that potentially could jam the mechanical actuation system. The solution is particularly suited for stable long-term storage of the device in it's pre-firing configuration.

In some embodiments, when in the pre-firing configuration, the dissolvable firing member is primarily acted upon by compression forces exerted onto the dissolvable firing member by the movable latch(es) being urged laterally towards the dissolvable firing member.

In some embodiments, the base member is defined by the capsule, such as by a capsule housing. In other embodiments, the base member is a member which is configured for movement relative to the capsule.

In some forms, the movable latch, or at least a part of the movable latch, is configured for movement orthogonally relative to the axis as it moves laterally when releasing the latching engagement between the blocking portion of the movable latch and the retainer portion. In other forms, the movable latch, or at least a part of the movable latch, is moved in a direction inclined with respect to a normal of the axis such as within +/−60 degrees from said normal, such as within +/−45 degrees, such as within +/−30 degrees, or such as within +/−15 degrees. In some forms the movable latch moves linearly, by a swivelling movement, or a combined linear and swivelling movement as the movable latch moves laterally when releasing the latching engagement between the blocking portion of the movable latch and the retainer portion.

In some embodiments the latch assembly is structured so that the movable latch, in the pre-firing configuration, exclusively or primarily exerts a compression force, such as laterally directed force, upon the dissolvable firing member.

In some embodiments, the second surface may be formed to define a support surface configured for interacting with the dissolvable firing member, wherein the second surface is disposed oppositely to the first surface.

In some further embodiments, the retainer portion is comprised by one of the base member and the actuation member. The movable latch may be formed as a deflectable latch comprised by the other of the base member and the actuation member, the deflectable latch being configured for lateral movement relative to the axis.

In some embodiments the second surface interacting with the dissolvable firing member is oriented with a surface normal directed generally laterally to the axis.

In some embodiments, the second surface is a radially inwards facing surface whereas the first surface is a radially outwards facing surface. In other embodiments, the second surface is a radially outwards facing surface whereas the first surface is a radially inwards facing surface.

In some configurations the dissolvable firing member is adjoined on two opposed surfaces by the movable latch on one of the two opposed surfaces and a load supporting surface on the other of the two opposed surfaces. Depending on the configuration the load supporting surface may be provided by a surface of the base member and/or by a surface of the actuation member.

In other embodiments, the movable latch is formed as an individual component arranged between the actuation member and the base member, and wherein the movable latch includes said first surface with a blocking portion, said second surface configured for interacting with the dissolvable firing member, and a third surface with a blocking portion. The first surface with the blocking portion is configured to engage a retainer portion of one of the base member and the actuation member, and the third surface with the blocking portion is configured to engage a retainer portion of the other of the base member and the actuation member.

In still other embodiments, the blocking portion of the movable latch is formed as a rigid part of the actuation member, wherein the actuation mechanism is so configured that a tilting movement of the actuation member is enabled relative to the axis, but wherein the dissolvable firing member in the pre-firing configuration prevents said tilting movement. In the firing configuration where the dissolvable firing member has become at least partially dissolved, the movable latch is allowed to move laterally so that the actuation member performs said tilting movement thereby releasing the latching engagement between the blocking portion of the movable latch and the retainer portion of the base to allow the energy source to fire the actuation member.

In embodiments where the movable latch is provided as an individual component, i.e. not formed unitarily with the base member or the actuation member, the medical device may be configured so that even after the device assumes the firing configuration, the movable latch is retained relative to the base member or the actuation member.

In some embodiments, in the pre-firing configuration, the at least one pair of a latch and a retainer portion is structured to maintain, i.e. releasably retain, the actuation member.

In some forms of the medical device, when assuming the pre-firing configuration, the energy source exerts a load on the actuation member, and the at least one pair of a latch and a retainer portion retains the actuation member relative to the base member against the load exerted by the energy source.

In other forms, when the medical device is taken into use, the energy source will not initially exert a load on the actuation member, but may be operated, such as by a user-initiated step, to provide said load.

In some further embodiments, the latch assembly is configured with an interface portion between the movable latch and the retainer portion, wherein the interface portion comprises an inclined surface portion that acts to transfer an axial load provided by the energy source, at least partly, into a lateral force urging the movable latch in a lateral direction.

In embodiments wherein the base member includes the retainer portion, the movable latch and/or the retainer portion of the base member may be formed to include an inclined surface, such as a chamfered surface. In embodiments wherein the actuation member includes the retainer portion, the movable latch and/or the retainer portion of the actuation member may be formed to include an inclined/chamfered surface.

In some forms the medical device comprises, in addition to the energy source of the actuation mechanism, a further energy source, i.e. a secondary energy source, which may provide a stronger force than said energy source of the actuation mechanism. In such form the actuation member may be structured to form an input member of a release trigger assembly. Subject to the firing configuration, the actuation member moves to cause triggering, i.e. release of energy or power from the secondary energy source. The secondary energy source may comprise one or more of a pre-energized energy source, such as a tensed spring or pressurized gas canister, and a pressure or force generating source that expands or inflates when triggered by movement of the actuation member. Non-limiting examples of force generating sources includes prime movers and gas generators which may involve a pair of reactants for generation of a gas. Non-limiting use examples for the secondary energy source includes a source for pushing or otherwise delivering a component, such as a payload or a sensor device, from the capsule to a site external to the capsule, such as a delivery site remote from the capsule.

In some embodiments the movable latch of the at least one pair of latch and retainer portion is configured for radial movement relative to the axis.

Example medical devices include devices wherein only a single pair of a latch and a retainer portion is provided. In other examples, a plurality of pairs of latch and retainer portions, such as two, three, four, five or more pairs of latch and retainer portions are provided, the pairs of latch and retainer portions being disposed equally around the axis.

In some embodiments said dissolvable firing member is common to all pairs of latch and retainer portions. In other embodiments, a plurality of individual dissolvable firing members are provided, such as where a dedicated dissolvable firing member is provided for each pair of latch and retainer portion.

In some exemplary embodiments the dissolvable firing member is arranged along the axis, and wherein the at least one pair of latch and retainer portion is disposed radially outside of the dissolvable firing member.

In other embodiments, the one or more dissolvable firing members is/are disposed in a ring-shaped configuration around the axis, the one or more dissolvable firing members encircling the at least one pair of latch and retainer portion.

In some examples of the medical device the capsule comprises one or more openings to allow a biological fluid, such as gastric fluid to enter the capsule for dissolving the dissolvable firing member.

In some forms the actuation member forms a ram configured for being fired for moving along the axis to apply pressure on an individual component of the medical device, wherein the individual component, in response to the ram being fired, is moved from a first position within the capsule to a second position, the second position being either within the capsule or partly or fully external to the capsule.

In other forms the actuation member forms a ram configured for being fired for moving along the axis from a first position within the capsule to a second position, the second position being either within the capsule or partly or fully external to the capsule.

The ram may be configured to carry or push one or more of a payload, a delivery member, and a sensor from a first position relative to the capsule to a second position relative to the capsule. In particular forms the ram itself forms one or more of a payload, a delivery member, and a sensor from a first position relative to the capsule to a second position relative to the capsule In some embodiments, the medical device is configured as a drug delivery device for delivery of a solid drug, an encapsulated solid, a liquid, a gel or a powder, or any combination thereof.

In some embodiments wherein the medical device is configured as a drug delivery device, the device comprises a therapeutic payload disposable or disposed in the capsule, wherein the therapeutic payload is configured for being expelled from the capsule into the lumen or the lumen wall. The actuation member may be provided in the form of a ram configured for being fired for moving along the axis to apply pressure on the therapeutic payload for expelling therapeutic payload from the capsule.

The drug delivery device may in some forms comprise a delivery member being associated with the therapeutic payload, the delivery member being configured for insertion into a mucosal lining of the lumen wall to deliver at least a portion of the therapeutic payload.

When the drug substance is in a flowable form, such as a liquid or powder, the drug may be expelled from the capsule through an outlet by means of jet action, i.e. expelling the drug at a penetration velocity allowing the drug substance to penetrate the lumen wall, such as the mucosal lining of the intestines or the stomach. By jet action, no delivery member is needed for penetrating the tissue. In such case, in some embodiments, the drug delivery device do not comprise any delivery member.

The delivery member may in some embodiments be provided as a solid delivery member formed partly or entirely from a preparation comprising the therapeutic payload, wherein the preparation is made from a dissolvable material that dissolves when inserted into tissue of the lumen wall.

In some forms the ram comprises an interface portion, wherein the delivery member attaches relative to the interface portion of the ram.

In such embodiments the ram may be fired to move the ram from a first position to a second position, and wherein the delivery member is configured for detachment relative to the interface portion of the ram when the ram assumes the second position.

In some configurations of the medical device according to the first aspect, the energy source is proved as a spring, such as a compression spring, the spring being strained or configured for being strained for powering the actuation member. However, other energy sources, such as a gas spring or a swelling member may be used in alternative embodiments.

In some forms the medical device defines an ingestible device suitable for swallowing by a patient and travelling into a lumen of a gastrointestinal tract of a patient.

Also, the medical device may be configured as a self-righting capsule, wherein when the self-righting capsule is at least partially supported by the tissue of the lumen wall, the self-righting capsule allows orienting in a pre-defined orientation prior to the medical device entering into the firing configuration.

In further embodiments according to the first aspect the medical device defines a capsule device comprising a capsule housing having an outside shape formed as a rounded object and defining an exterior surface. The capsule device further comprises a solid delivery member having a needle or dart-shaped form and being formed partly or entirely from a preparation comprising the therapeutic payload, wherein the preparation is made from a dissolvable material that dissolves when inserted into tissue of the lumen wall. The actuation member is formed as a ram that comprises an interface portion, wherein the solid delivery member is held or attached relative to the interface portion of the ram. The capsule device is configured as a self-righting capsule having a geometric center and a center of mass offset from the geometric center along the axis, wherein when the capsule device is supported by the tissue of the lumen wall while being oriented so that the centre of mass is offset laterally from the geometric center the capsule device experiences an externally applied torque due to gravity acting to orient the capsule device with the axis oriented along the direction of gravity to enable the solid delivery member to interact with the lumen wall at the target location. Upon entering into the firing configuration, the ram moves along the axis thereby inserting the solid delivery member into tissue. Subsequent to insertion, the solid delivery member may at least partially dissolve and release one or more APIs and/or other therapeutic agents into the tissue.

Non-limiting examples of a self-orienting device may include devices configured for firing when the device is located in the stomach lumen of a patient. Other examples may include devices configured for firing when the device is located in the small intestines or the large intestines.

In a second aspect of the invention a drug delivery device suitable for insertion into a lumen of a patient, the lumen having a lumen wall, is provided. The drug delivery device comprises a capsule sized to be inserted into the lumen, a therapeutic payload disposable in the capsule, the therapeutic payload configured for being expelled from the capsule into the lumen or the lumen wall, a ram configured for being fired for moving along an axis to apply pressure on the therapeutic payload for expelling therapeutic payload from the capsule, and an energy source associated with the ram for powering the ram to expel the therapeutic payload. The capsule and the ram comprises at least one pair of a latch and a retainer portion structured to maintain the ram in a pre-firing configuration. For each pair of latch and retainer portion the drug delivery device defines a dissolvable firing member, the dissolvable firing member being at least partially dissolved in a fluid, such as a biological fluid, a retainer portion comprised by one of the capsule and the ram, and a deflectable latch comprised by the other of the capsule and the ram. The deflectable latch is configured for lateral movement relative to the axis, and the deflectable latch defines a first surface with a blocking portion, and a support surface disposed oppositely to the first surface and configured for interacting with the dissolvable firing member. In the pre-firing configuration, the blocking portion of the deflectable latch engages the retainer portion in a latching engagement, and the support surface of the deflectable latch interacts with the dissolvable firing member to restrict movement of the deflectable latch thereby preventing release of the latching engagement. In a firing configuration wherein the dissolvable firing member has become at least partially dissolved, the deflectable latch is allowed to move thereby releasing the latching engagement between the blocking portion of the deflectable latch and the retainer portion to allow the energy source to fire the ram.

By this arrangement, instead of having a dissolvable member that carries the whole power or load of the energy source, the dissolvable part is designed to simply block a mechanical actuation system. The mechanical actuation system may be designed to rely on parts made from a suitable high-strength material, such as plastic, and do not leave any undissolved pieces that potentially could jam the mechanical actuation system.

Any of the following characteristics may be included by any of the device embodiments according to the first and the second aspects thus providing further beneficial embodiments.

In exemplary embodiments, the deflectable latch is configured for radial movement relative to the axis. In some examples the firing axis and the ram movement is linear. In other exemplary embodiments, the firing axis may be not linear, e.g. the firing trajectory of the ram may be arcuate or curved, or may include arcuate or curved trajectories. In accordance herewith, the latch may be configured for lateral movement relative to the trajectory of the ram to release the ram.

In exemplary embodiments a plurality of pairs of latch and retainer portions, such as two, three, four, five or more pairs of latch and retainer portions are provided, the pairs of latch and retainer portions being disposed equally around the axis.

In some embodiments said dissolvable firing member is common to all pairs of latch and retainer portions.

In further embodiments, the dissolvable firing member is arranged along the axis, wherein the at least one pair of latch and retainer portion is disposed radially outside of the dissolvable firing member.

In other variants one or more dissolvable firing members is/are disposed, such as in a ring-shaped configuration around the axis, wherein the one or more dissolvable firing members encircle the at least one pair of latch and retainer portion.

The capsule may comprise one or more openings to allow gastric fluid to enter the capsule for dissolving the dissolvable firing member(s).

In some embodiments, the drug delivery device comprises a delivery member being associated with the therapeutic payload, the delivery member being configured for insertion into the lumen wall to deliver at least a portion of the therapeutic payload. The delivery member may have an outer shape as a needle, or may be provided as an injection needle.

The delivery member may be shaped to penetrate tissue of the lumen wall and having a tissue penetrating end and an end opposite the tissue penetrating end.

In exemplary embodiments the ram comprises an interface portion wherein the delivery member attaches relative to the interface portion of the ram.

In some embodiments, the ram is fired to move the ram from a first position to a second position, wherein the delivery member is configured for detachment relative to the interface portion of the ram when the ram assumes the second position.

In some further embodiments, the delivery member is a solid delivery member formed partly or entirely from a preparation comprising the therapeutic payload, and wherein the preparation is made from a dissolvable material that dissolves when inserted into tissue of the lumen wall.

In other embodiments having a delivery member, the delivery member comprises an injection needle, and wherein the therapeutic payload forms a liquid or powder being expellable through the injection needle.

In some embodiments, the energy source is or comprises at least one spring configured as a drive spring. Exemplary springs include a compression spring, a torsion spring, a leaf spring or a constant-force spring. The spring may either be strained or configured for being strained for powering the ram. Other non-limiting exemplary types of energy sources include compressed gas actuators or gas generators. In some embodiments, in the pre-firing configuration, the energy source exerts a load onto the ram thereby biasing the ram along the axis.

In exemplary embodiments, the drug delivery device is configured as an ingestible device suitable for swallowing by a patient and travelling into a lumen of a gastrointestinal tract of a patient, such as the stomach or the small intestines. The capsule of the device may be shaped and sized to allow it to be swallowed by a subject, such as a human.

In still further exemplary embodiments, the drug delivery device is configured as a self-righting capsule, wherein when the self-righting capsule is at least partially supported by the tissue of the lumen wall, the self-righting capsule orients in a direction to allow the delivery member to be inserted into the lumen wall to deliver at least a portion of the therapeutic payload into the tissue.

By the above arrangements an orally administered drug can be delivered safely and reliably into the stomach or intestinal wall of a living mammal subject. The drug substance may e.g. be in the form of a solid, an encapsulated solid, a liquid, a gel or a powder, or any combination thereof.

In a third aspect of the invention a medical device is provided suitable for insertion into a lumen of a patient, the lumen having a lumen wall. The medical device comprises a housing sized to be inserted into the lumen, a ram configured for being fired for moving along an axis to perform an actuation operation, and an energy source associated with the ram for powering the ram. The housing and the ram comprises at least one pair of a latch and a retainer portion structured to maintain the ram in a pre-firing configuration. For each pair of latch and retainer portion the medical device defines a dissolvable firing member, the dissolvable firing member being at least partially dissolved in a fluid, such as a biological fluid, a retainer portion comprised by one of the housing and the ram, and a deflectable latch comprised by the other of the housing and the ram. The deflectable latch is configured for lateral movement relative to the axis, and the deflectable latch defines a first surface with a blocking portion, and a support surface disposed oppositely to the first surface and configured for interacting with the dissolvable firing member. In the pre-firing configuration, the blocking portion of the deflectable latch engages the retainer portion in a latching engagement, and the support surface of the deflectable latch interacts with the dissolvable firing member to restrict movement of the deflectable latch thereby preventing release of the latching engagement. In a firing configuration wherein the dissolvable firing member has become at least partially dissolved, the deflectable latch is allowed to move thereby releasing the latching engagement between the blocking portion of the deflectable latch and the retainer portion to allow the energy source to fire the ram.

In some embodiments according to the third aspect, the housing defines a capsule, such as a capsule shaped and sized to be ingested by a patient. Any combinations of the embodiment features mentioned in accordance with the first aspect and the second aspect may in further embodiments be provided in combination with the features according to the third aspect.

Whereas this disclosure mainly refers to drug delivery from a capsule device to a lumen or lumen wall, the invention in its broadest aspect is not limited to drug or substance delivery, but rather concerns a particular actuation assembly. The capsule device comprising the actuation mechanism according to the present invention may be configured for other uses. Non-limiting uses include obtaining one or more samples from a body lumen, e.g. by including a sample taking device for introducing a sample from a body lumen or lumen wall into the capsule device, and delivering a monitoring or analysis device, e.g. by disposing or positioning a sensor device from the capsule device into the lumen or lumen wall.

As used herein, the terms "drug" or "payload" is meant to encompass any drug formulation capable of being delivered into or onto the specified target site. The drug may be a single drug compound or a premixed or co-formulated multiple drug compound. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid, powder or liquid form. Specifically, the drug may be an insulin or a GLP-1 containing drug, this including analogues thereof as well as combinations with one or more other drugs.

BRIEF DESCRIPTION OF THE DRAWINGS

In the following embodiments of the invention will be described with reference to the drawings, wherein:

FIG. 6b shows schematically a cross-sectional perspective view of the third embodiment sub-assembly shown in FIG. 6a.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Figure 1A:
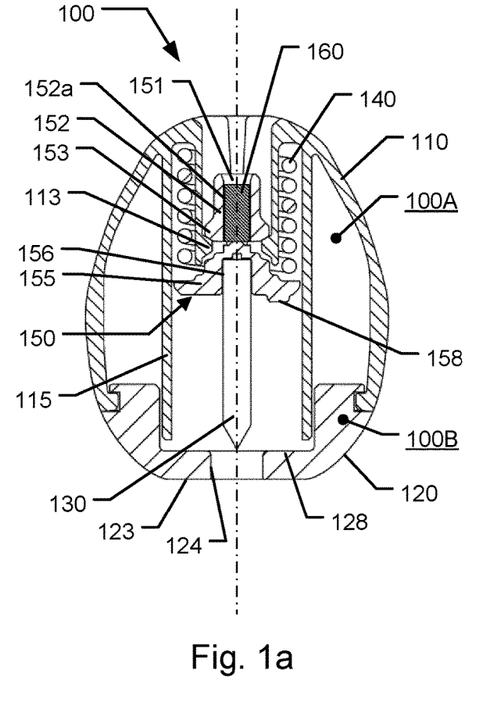
FIGS. 1a and 1b each shows a cross-sectional front view of a first embodiment of a capsule device in accordance with the invention configured for solid dose delivery, the device assuming a pre-firing configuration and a firing configuration, respectively.
Figure 1B:
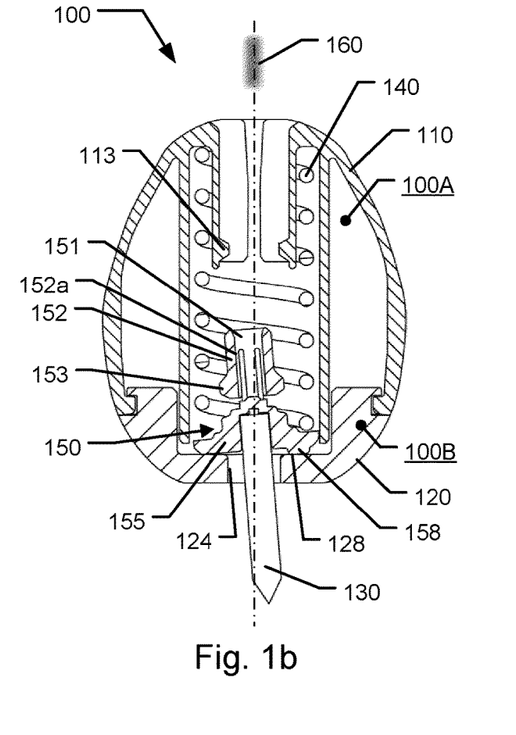

With reference to FIGS. 1a and 1b a first embodiment of a drug delivery device in accordance with an aspect of the invention will be described, the embodiment being designed to provide a capsule device 100 having a desired firing principle for deployment of a solid dose from a solid dose capsule device. The disclosed embodiment relates to a capsule device 100 suitable for being ingested by a patient to allow the capsule device to enter the stomach lumen, subsequently to orient relative to the stomach wall, and finally to deploy a solid dose payload for insertion at a target location in tissue of the stomach wall. For the capsule device 100 the general principle for orienting the capsule relative to the stomach wall may utilize any of the principles disclosed in WO 2018/213600 A1.

The ingestible self-righting capsule device 100 comprises a first portion 100A having an average density, a second portion 100B having an average density different from the average density of the first portion 100A. The capsule device 100 accommodates a payload portion 130 for carrying an agent for release internally of a subject user that ingests the article. In the shown embodiment, the average density of capsule device prior to deployment is larger than that of gastrointestinal fluid, enabling the capsule device to sink to the bottom of the stomach lumen. The outer shape of the self-righting article is a gomboc shape, i.e. a gomboc-type shape that, when placed on a surface in any orientation other than a single stable orientation of the shape, then the shape will tend to reorient to its single stable orientation.

The capsule device shown includes an upper (proximal) capsule part 110 which mates and attaches to a lower (distal) capsule part 120. The upper capsule part 110 and the lower capsule part 120 together forms the capsule of the device. The capsule defines an interior hollow which accommodates the payload portion 130, a ram 150 which holds and drives forward the payload portion 130, and a firing and propulsion mechanism configured to fire and drive forward the ram with the payload for drug delivery. The payload portion 130 is oriented along a firing axis and configured for movement along the firing axis. In the shown embodiment, the upper and lower capsule parts 110, 120 form rotation symmetric parts which are symmetric around the firing axis. In the drawings, the device is oriented with the firing axis pointing vertically, and with the payload portion 130 pointing vertically downwards towards an exit hole 124 arranged centrally in the lower capsule part 120, the exit hole allowing the payload portion 130 to be transported through exit hole and moved outside the capsule device 100. The lower part 120 includes a tissue engaging surface 123 which is formed as a substantially flat lower outer surface surrounding the exit hole 124.

Regarding suitable materials for the capsule parts for the embodiment shown in FIGS. 1a and 1b, the upper part may suitably be made from a low-density material, such as polycaprolactone (PCL), whereas the lower part 120 may be suitably made from a high-density material, such as 316L stainless steel.

In the shown embodiment, due to the density distribution of the entire capsule device 100, and due to the outside shape of the device, the capsule device 100 will tend to orient itself with the firing axis substantially perpendicular to the surface (e.g., a surface substantially orthogonal to the force of gravity, a surface of a tissue such as the wall of the gastrointestinal tract). Hence, the capsule device tends to orient relative to the direction of gravity so that the tissue engaging surface 123 faces vertically downward.

The interior of the upper capsule 110 includes a sleeve shaped ram guiding structure 115 which extends concentrically with the firing axis from the upper part of the upper capsule part 110 towards a ram stop surface 128 defined by an inner bottom surface formed in the lower capsule part 120, i.e. a proximally facing stop surface. Further, in the shown embodiment, a second sleeve shaped structure extends concentrically with the firing axis and radially inside the ram guiding structure 115 from the upper capsule part 110 and downwards along the firing axis. The second sleeve shaped structure serves as a retainer structure for retaining the ram 150 against the drive force emanating from a strained drive spring 140 arranged within the capsule. In the shown embodiment, the retainer structure has a radially inwards protruding retainer portion 113 arranged at the lower end of the retainer structure. In the shown embodiment, the retainer portion 113 is provided as two opposed radially inwards protruding arc-shaped protrusions.

In the first embodiment shown in FIGS. 1a and 1b, payload portion 130 defines a solid delivery member formed entirely or partly from a preparation comprising the therapeutic payload. In the shown embodiment, the solid delivery member is formed as a thin cylindrical rod shaped to penetrate tissue of the lumen wall, the cylindrical rod having a tissue penetrating end and trailing end opposite the tissue penetrating end. The tissue penetrating end of the rod is pointed to facilitate easy insertion into tissue of the lumen wall whereas the trailing end, in the shown embodiment, defines a truncated cylinder cut off by a 90-degree cut. A non-limiting example of a drug suitable for delivery by capsule device 100 is dried compressed API such as insulin.

The ram 150 comprises an upper retaining part 151 and a lower interface part 155 configured for holding the trailing end of the payload portion 130 in place. In the shown embodiment, the interface part includes a downward open bore that receives the trailing end of the payload portion 130 in a way so that the payload portion 130 is firmly attached within the bore. The lower interface part 155 further defines an annular outer flange having a diameter slightly smaller than the diameter of the ram guiding structure 115. In the shown embodiment, the ram 150 is movable, while being guided for axial movement by the ram guiding structure 115, from a pre-firing configuration shown in FIG. 1a to a firing configuration shown in FIG. 1b.

With regard to the above-mentioned drive spring 140, in capsule device 100, a helical compression spring is arranged coaxially with the firing axis. The proximal end of drive spring 140 is seated against a spring seat of upper capsule part 110, i.e. located radially between the ram guiding structure 115 and the retainer structure. The distal end of drive spring 140 is seated against a spring seat formed by a proximal surface of the flange defined by the lower interface part 155 of the ram 150. As part of assembling the capsule device 100 the drive spring 140 has been energized by axially compressing the drive spring 140 between the two spring seats. Hence, the ram is initially under load from drive spring, such as in the order of 10-30 N. Alternatives to using a compression spring for generating the drive force, other spring configurations may be used to energize the capsule device 100, such as a torsion spring, a leaf spring, a constant-force spring or similar. In further alternatives, a gas spring or a gas generator may be used.

The upper retaining part 151 of the ram 150 includes deflectable latches provided in the form of two deflectable arms 152 which extend in distal direction from the upper end of the ram towards the exit opening 124, each arm being resiliently deflectable in the radial inwards direction. The end of each deflectable arm 152 includes a blocking portion 153 protruding radially outwards from the resilient arm. In the pre-firing configuration shown in FIG. 1a, a distal surface of each of the blocking portions 153 engage a proximal surface of a corresponding one the retainer portions 113. As the blocking portions 153 initially are located proximally to the retainer portions 113 the ram 150 cannot be moved distally past the retainer portions 113 unless the deflectable arms 152 become sufficiently deflected in the radially inwards direction.

In the pre-firing configuration a dissolvable pellet 160 is arranged between the two deflectable arms 152 so that radial opposing surfaces of the pellet 160 engage a radially inwards facing support surface of the two deflectable arms 152, shown as second surface 152a. In the shown embodiment, the pellet 160 is arranged in a compartment inside the upper capsule part 110, and a proximally arranged upper opening in upper capsule part 110 facilitates fluid exposure to the dissolvable pellet when the capsule device is submerged in a fluid. In the pre-firing configuration shown in FIG. 1a, as the dissolvable pellet 160 assumes a non-compressible state the pellet prevents the two deflectable arms from bending inwards. However, upon exposure to a fluid, such as gastric fluid present in the stomach of a patient, the dissolvable pellet starts to dissolve. The pellet 160 is designed to become gradually dissolved so that after a predefined activation time, the pellet has been dissolved to a degree allowing the two deflectable arms 152 to become sufficiently deflected inwards enabling the blocking portions 153 of ram 150 to be moved distally past the retainer portions 113. In this condition, i.e. the firing configuration, the ram 150 has been fired with the load of the drive spring 140 forcing the ram 150 distally towards the exit hole 124. The ram 150 drives the payload portion 130 distally with the payload tip protruding initially from the capsule, and gradually pressing out the remaining payload portion 130. The forward movement of the payload portion 130 is halted when ram 150 bottoms out in the lower capsule part 120. This condition is depicted in FIG. 1b.

In the shown embodiment, the interface between the retainer portions 113 and the blocking portions 153 is sloped/inclined by approximately 30° so that the deflectable arms will slide inwards when the dissolvable pellet is dissolved. The angle determines the shear forces on the pellet and to which degree the deflectable arms will tend to slide inwards when subjected to the load force. In connection with the acceleration length of the ram when fired, the optimal angle is 0°, but it requires a much higher spring force to activate such configuration. For the sloped portions, in other embodiments, angles other than 30° may be used.

FIG. 1b reveals that, in the shown embodiment, the ram 150 and the payload portion 130 may enter an orientation that is somewhat tilted relative to the firing axis. This effect is obtained by a tilting mechanism that tilts the ram 150 upon the ram reaching its end destination. However, this shown condition is somewhat hypothetical, as it is only representative for a capsule device being fired into the open, or with the payload portion being fired into a fluid.

In situation of intended use, the payload portion 130 is inserted into tissue of the lumen wall where it will anchor generally in a direction along the firing axis. However, at the end of the drive stroke, and due to the tilting action of the ram 150, a bending torque is applied onto payload portion 130 tending to break or otherwise release the connection between payload 130 and ram 150. This effect is introduced to enable the payload portion 130 to become forcedly separated from the ram 150 to prevent that payload portion 130 becomes withdrawn from the tissue after it has been properly lodged within the tissue.

At this point the capsule device 100 has delivered the intended dose and will release relative to the deposited payload portion 130 which rests inside the tissue wall. Subsequently, the remaining parts of the capsule device will travel out through the digestive system of the user and be disposed of.

If the payload 130 where still fixedly connected to ram 150, and thus also to the remaining parts of the capsule device 100, the likelihood that payload portion would become retracted from the tissue by movements of the capsule device relative to the target location would be high.

In the shown embodiment, the tilting motion of ram 150 upon reaching the end destination is obtained by forming an eccentrically arranged protrusion 158 on the distally facing surface of interface part 155 of ram 150. As proximally facing ram stop surface 128 defined by the inner bottom surface formed in the lower capsule part 120 is planar, and oriented orthogonally to the firing axis, a tilting effect is obtained as ram 150 meets the ram stop surface 128. As will be discussed further below, the tilting effect may be obtained by a variety of alternative geometrical designs. Also, although not depicted in this disclosure, a guide system between ram guiding structure 115 and the ram 150 may alternatively be formed to obtain a similar tilting effect. It should also be noticed that in other embodiments of a capsule device, the tilting effect may be omitted.

For the dissolvable member discussed above, i.e. the dissolvable pellet 160 forming a dissolvable firing member, different forms and compositions may be used. Non-limiting examples include pellets made from Sorbitol or Microcrystalline cellulose (MCC). Other non-limiting examples include injection moulded Isomalt pellets, compressed granulate Isomalt pellets, compressed pellets made from a granulate composition of Citrate/NaHCO3, or compressed pellets made from a granulate composition of Isomalt/Citrate/NaHCO3. A non-limiting exemplary size of a dissolvable pellet is a pellet which at the time of manufacturing measures Ø1×3 mm.

In the shown example of ram 150 the upper retaining part 151 is formed as a chamber wherein the dissolvable pellet 160 is received within the chamber having a tight fit. In the shown embodiment, the central upper part of capsule device 100 includes a single opening for introducing stomach fluid within the capsule. In other embodiments, the capsule may include other design of fluid inlet openings such as multiple openings distributed around the capsule. In some designs, the payload portion 130 is accommodated in a chamber that is fluidly sealed from the chamber of the dissolvable pellet. Also, the exit hole 124 may include a seal preventing moisture from entering the payload portion chamber prior to firing of the capsule device 100.

Figure 2:
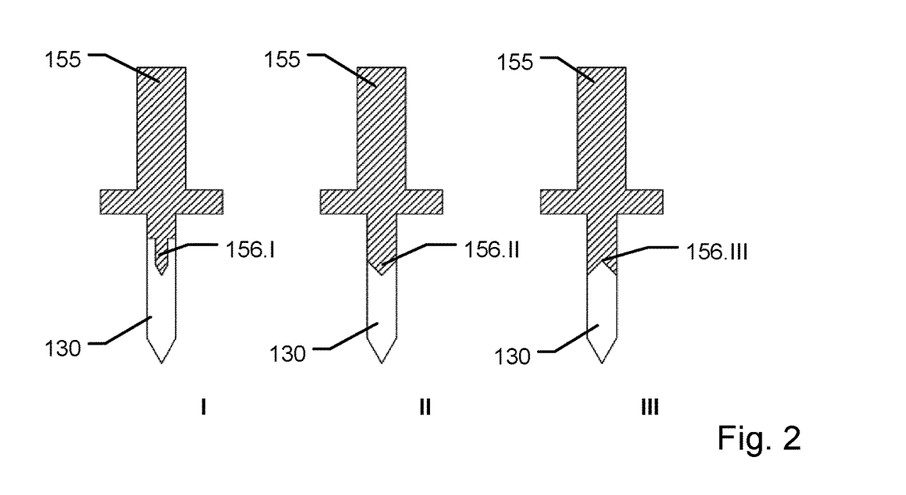
FIG. 2 shows schematically three different configurations of an assembly of a ram and a solid dose delivery member for use in a capsule device according to an aspect of the invention.

Turning now to FIG. 2, three alternative suitable designs for a ram and payload portion are schematically depicted, each design obtaining a desired attachment between ram 150 and payload portion 130 and enabling a desired controlled detachment of payload portion 130 from ram 150.

Design no. I includes a ram 150 having a central pin 156.I extending from lower interface part 155 of the ram 150. Payload portion 130 is correspondingly formed with a central opening configured for receiving central pin 156.I.

Design no. II includes a ram 150 having a central conical protrusion 156.II extending from lower interface part 155 of the ram 150. Payload portion 130 is correspondingly formed with a central conical depression configured for mating with and receiving conical protrusion 156.II.

Design no. III includes a ram 150 having a central conical depression 156.III at the distal facing surface of lower interface part 155 of ram 150. Payload portion 130 is correspondingly formed with a central conical protrusion configured for mating with and receiving conical protrusion 156.III.

The above described four different variants of interfaces between the payload portion 130 and the ram 150 are only exemplary and other configurations may be used instead. The detachable attachment between the payload portion and the ram may be obtained by using a friction or press fit. Alternatively, an adhesive may be used at the interface, such as sucrose.

Still alternatively, the attachment may be obtained by initially wetting the payload portion and utilizing inherent stiction between the ram and the payload portion. In situation of use, upon the ram reaching its final destination, detachment may occur at the interface between the payload portion and the ram. In other embodiments, a desired detachment may be obtained by detaching a major portion of the payload portion from the remaining payload portion being still adhered or fastened to the ram. In some embodiments, the payload portion includes a weakened point which determines the point of separation. In still further embodiments, as discussed further below, the ram and the payload portion may be formed as a unitary component all made of a composition containing API, and wherein the intended payload portion to be pushed out from capsule device is separated from the ram portion. Also, in alternative embodiments, the payload may act as a ram by itself to be fully transported away from the capsule device.

Figure 3:
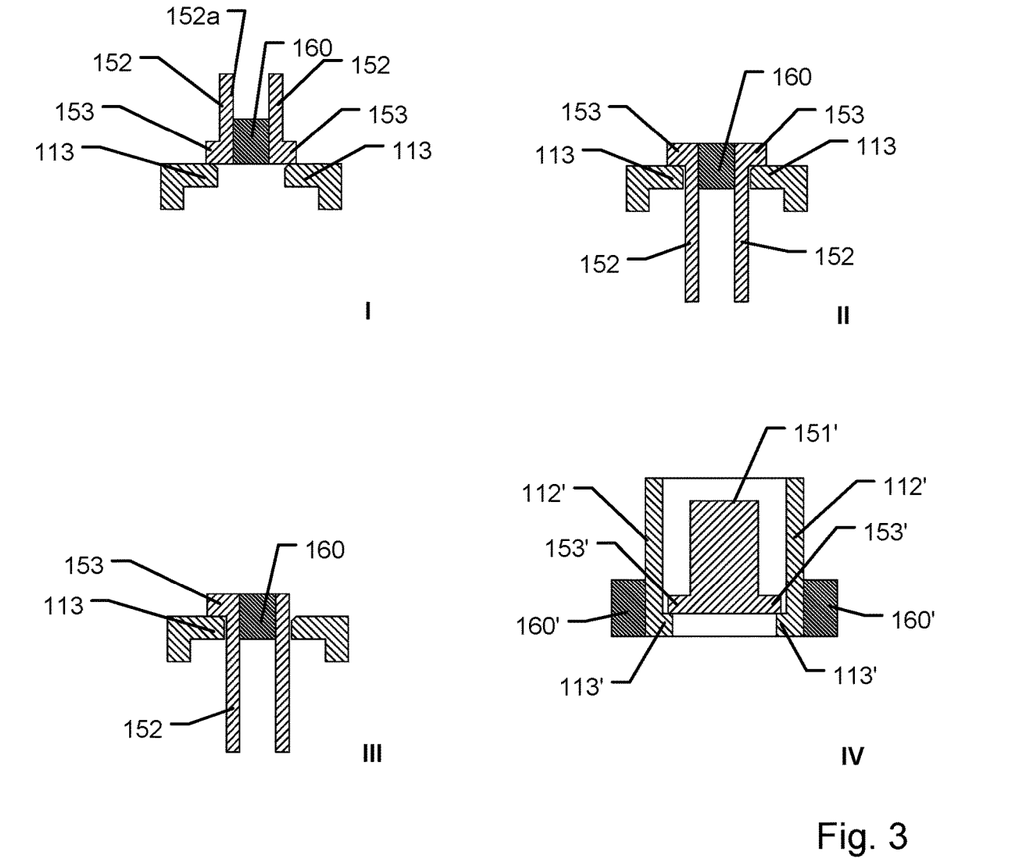
FIG. 3 shows schematically four different configurations of pairs of deformable latch and retainer portion assemblies for use in firing a ram in a capsule device according to the invention.

FIG. 3 schematically shows four additional designs for one or two pairs of deflectable latch and retainer configurations to be used in further exemplary capsule devices. As will be readily apparent, the number of deflectable latch elements, the location and the orientation of deflectable latch elements, the number and configuration of dissolvable firing members as well as the design of the ram may be varied in agreement with an aspect of the present invention while still obtaining firing mechanisms having a superior mode of action. For simplicity, only the upper retaining part 151 of ram 150 has been shown. Likewise, only the retainer structure of the capsule parts have been shown.

In FIG. 3, design no. I a retainer portion having upwardly extending retaining structure 113 to cooperate with blocking elements on two deflectable arms 152, and second surface 152*a* is shown. In this design, a ram and a dissolvable firing member 160 having an overall structure as shown in FIG. 1*a* may be used.

Design no. II also includes an upwardly extending retaining structure 113 wherein a major portion of the ram is suspended. In this embodiment, the ram includes proximally extending delectable arms having blocking elements on the proximal ends of the deflectable arms 152, and wherein the proximal ends of the arms are designed to flex radially inwards when a centrally located dissolvable firing member 160 is sufficiently dissolved.

The figure depicting design no. 3 shows a related configuration but wherein the ram only includes a single deflectable arm. In this design a non-deflectable structure is arranged on the side of the dissolvable firing member 160 on the side facing away from the single deflectable arm. The non-deflectable structure continuously supports the dissolvable firing member 160 on one side thereof whereas the opposing side makes room for the single deflectable latch arm to move radially inwards and pass the retainer portion 113.

Finally, design no. IV schematically shows an example wherein the deflectable latch and the retainer portions have swapped places. In this design the ram includes an upper retainer portion 151' with retainer portions 153' which are designed not to exhibit any flexure during firing of the actuation mechanism. The retaining structure (associated with either the upper capsule part or the lower capsule part) instead includes two deflectable latches in the form of distally extending deflectable latch arms 112', each having a blocking portion 153' at its most distal end. Each deflectable arm 112' is configured to engage a respective dissolvable firing member 160'. Said respective dissolvable firing members 160' may thus be provided as a common ring-shaped member or be provided as a plurality of separate members arranged in a ring-configuration around the firing axis. As noted above, in some embodiments, the payload may act as a ram by itself to be partly or fully disconnected from the remainder of the capsule device. Such API based ram may include retainer portions which are designed not to exhibit any flexure during firing of the actuation mechanism where the retainer portions are allowed to pass cooperating deflectable latches associated with the housing of the capsule, e.g. the upper or lower capsule parts.

Figure 4:
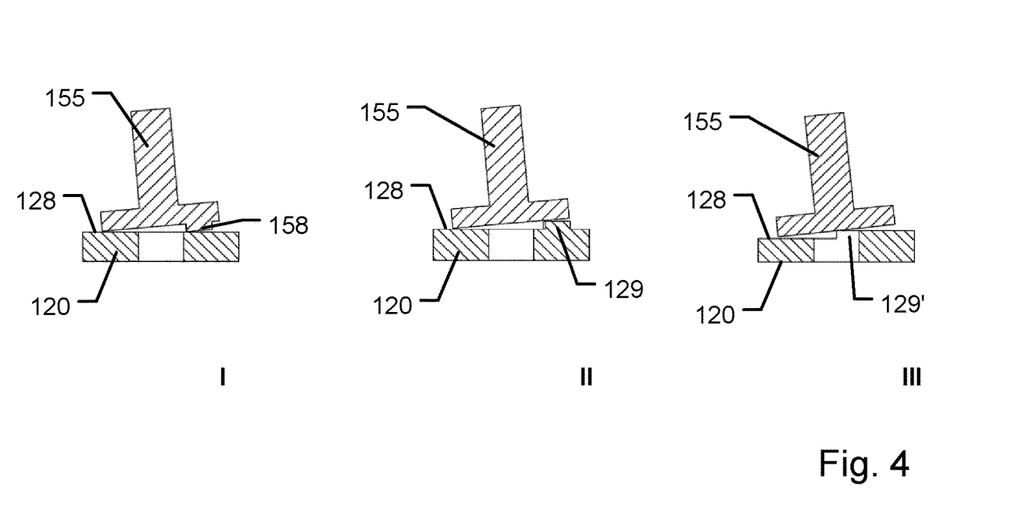
FIG. 4 shows schematically three different configurations of a capsule and ram assembly to enable solid dose delivery detachment between a solid delivery member and a ram.

FIG. 4 schematically shows three designs for obtaining the tilting effect of the ram 150 as described above. In design no. I, an eccentrically disposed protrusion 158 is formed on the distally facing surface of interface part 155 of ram 150, i.e. the surface facing the ram stop surface 128. In design no. II, an eccentrically disposed protrusion 129 on the ram stop surface 128 is located to protrude in the proximal direction towards the lower surface of the interface part 155 of ram 150. In the variant shown as design III the ram stop surface 128 is formed as a stepped surface 129', i.e. comprising two or more levels that induces a tilting movement of ram 150 as it reaches the ram stop surface 128. It is to be noted that other ways of tilting the ram upon reaching the final destination than shown schematically in FIG. 4 may be carried out by other means.

Figures 5A, 5B:
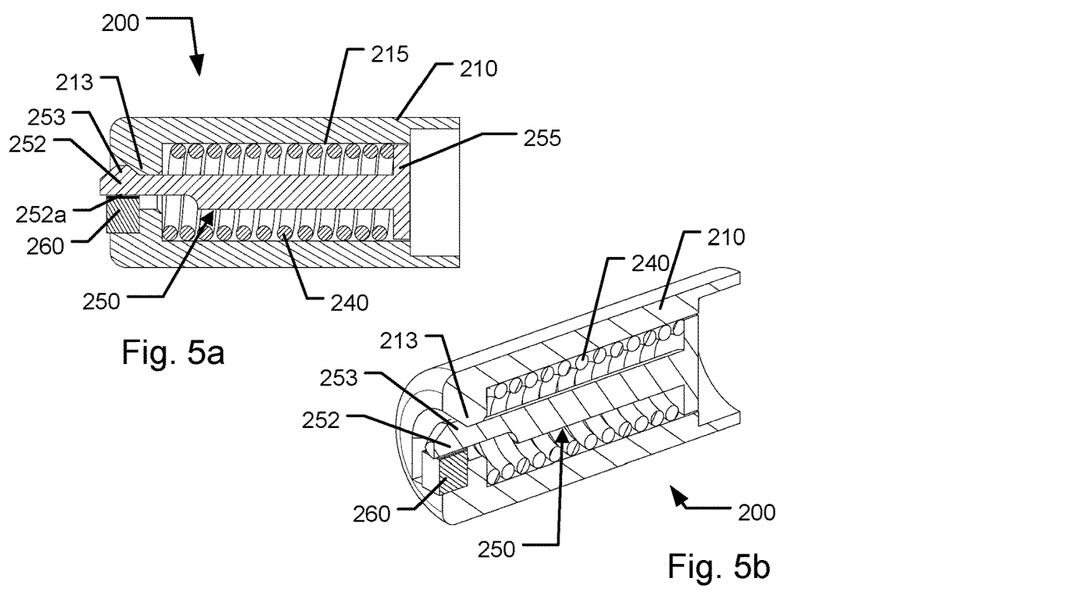
FIG. 5a shows schematically a cross-sectional side view of a sub-assembly of a second embodiment capsule device, the device configured for releasably retaining an actuation member, wherein the figure depicts a pre-firing configuration.
FIG. 5b shows schematically a cross-sectional perspective view of the second embodiment sub-assembly shown in FIG. 5a, FIG. 6a shows schematically a cross-sectional side view of a sub-assembly of a third embodiment capsule device, the device being configured for releasably retaining an actuation member, wherein the figure depicts a pre-firing configuration.

With reference to FIGS. 5*a* and 5*b*, a sub-assembly 200 of a second embodiment of a medical device in accordance with an aspect of the invention will next be described, the second embodiment being designed to provide a capsule device having a desired actuation mechanism for moving an actuation member, such as a ram, from a first position to a second position. Relative to the actuation mechanism shown in the first embodiment, the actuation mechanism of the second embodiment utilizes the same general working principle, however with a latch element 252 which does not rely on a deflectable component, but rather forms a rigid part of the actuation member.

The depicted second embodiment relates to a capsule device suitable for being introduced or to enter into a lumen of the human body. For simplicity, only components relevant for the actuation mechanism are shown, and the further components of the capsule device will not be extensively described.

The capsule device according to the second embodiment includes a sub-assembly 200 as depicted in FIG. 5*a* comprising a capsule housing part 210 which serves as a base member, an actuation member 250, a drive spring 240 in form of a energized compression spring, and a dissolvable pellet or firing member 260. A further capsule housing (not shown) is intended to be coupled to the right-hand side of capsule housing part 210 to form an elongated ingestible capsule. Actuation member 250, taking the form of an elongated plunger or ram, is mounted for axial movement along an axis extending lengthwise through a cylindrical opening 215 of capsule housing part 210. The actuation member 250 is configured for sliding axial movement inside the cylindrical opening 215 from a pre-firing configuration which is shown (a proximal position), and in an axially distal direction into a fired configuration (not shown) where the plunger would have moved to the right in FIG. 5*a* (a distal position). In the pre-firing configuration the compression spring 240 exerts a load onto the actuation member which urges the actuation member 250 distally towards the fired configuration. During release of the actuation mechanism, the actuation member 250 is furthermore movable by a tilting movement relative to the axis into a firing configuration which releases the actuation member for axial movement.

The distal end portion of the actuation member 250 forms a piston 255 which is received in close fitting relationship with the cylindrical opening 215 so that the piston is able to slide within cylindrical opening 215. From the piston 255 a reduced diameter shaft extends towards the proximal end of the actuation member 250. The proximal end of the reduced diameter shaft includes a radially outwards facing surface with a blocking portion 253 protruding radially outwards in a particular lateral direction (in the drawing shown protruding upwards). The blocking portion 253 serves as a latch which is laterally movable. Located radially opposite blocking portion 253, but at the same axial position, the radially outwards facing second surface 252a of the shaft includes a stepped down surface configured to cooperate and engage with a dissolvable firing member or pellet 260.

In the shown embodiment, the dissolvable firing member 260 is formed as a rectangular box-shaped object. A constriction is provided inside the cylindrical opening 215 at a position close to the most proximal end thereof. The constriction includes a recessed area wherein the dissolvable firing member 260 is received. An assembly of the capsule housing part 210 and the dissolvable firing member 260 forms a keyhole through which the shaft of the actuation member protrudes while enabling no or only little lateral movement of the shaft inside the keyhole. The constriction forms a first retainer portion 213 inside the capsule housing 210, in the depicted state located distally from blocking portion 253 of the shaft. In the shown embodiment, both the blocking portion 253 and the first retainer portion 213 include mating inclined surfaces which lies in intimate contact with each other.

In the pre-firing configuration shown in FIGS. 5a and 5b, the dissolvable firing member 260 radially supports the proximal portion of the actuation member 250 in an almost central position where the stepped down surface of the shaft is located, i.e. in a manner where the actuation member is aligned generally coaxial with the axis. The blocking portion 253 of the shaft performs as a latch that engages the first retainer portion 213 in a latching engagement. Upon the dissolvable firing member 260 becoming exposed to a fluid, such as stomach or intestinal fluid, the dissolvable firing member becomes at least partially dissolved inside the recessed area of the constriction. This enables lateral movement the proximal end of the shaft in a radial direction away from the first retainer portion 213 (i.e. downwards in FIG. 5a), said movement causing a tilting of the actuation member 250 relative to the axis. The lateral movement is due to the drive spring 240 exerting a distally directed force on the actuation member 250, and due to the mating inclined surfaces of the blocking portion 253 and the first retainer portion 213.

Upon sufficient dissolvement of the dissolvable firing member 260, the blocking portion 253 will be able to pass the first retainer portion 213 in which case the device assumes the firing configuration. This causes the drive spring 240 to expand freely until the actuation member 250 reaches the second position and the device sub-assembly 200 assumes the fired configuration.

Figures 6A, 6B:
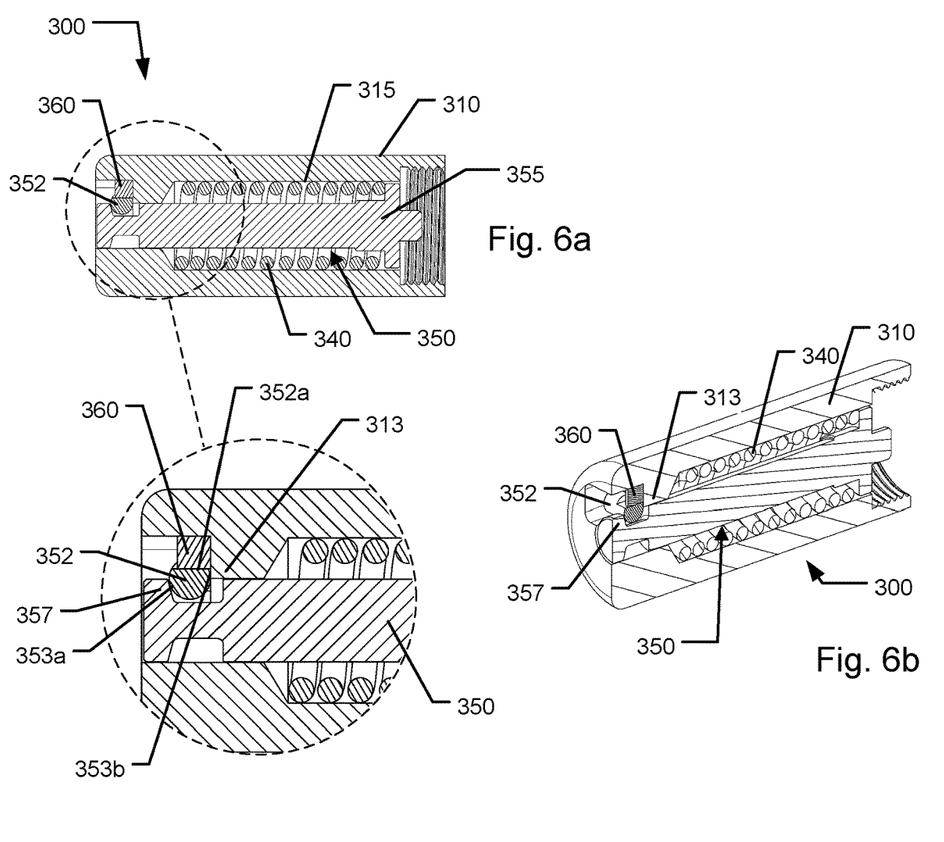

Turning now to FIGS. 6a and 6b, a sub-assembly 300 of a third embodiment of a medical device in accordance with an aspect of the invention will next be described, the third embodiment being designed to provide a capsule device having a desired actuation mechanism for moving an actuation member, such as a ram, from a first position to a second position. Relative to the actuation mechanisms shown in the first and second embodiment, the actuation mechanism of the third embodiment utilizes the same general working principle, however with a latch element which forms an individual member separate from the base member and the actuation member.

The depicted third embodiment relates to a capsule device suitable for being introduced or to enter into a lumen of the human body. For simplicity, only components relevant for the actuation mechanism are shown, and the further components of the capsule device will not be extensively described.

The capsule device according to the third embodiment includes a sub-assembly 300 as depicted in FIG. 6a comprising a capsule housing part 310 which serves as a base member, an actuation member 350, a drive spring 340 in form of an energized compression spring, a latch member 352, and a dissolvable pellet or firing member 360. A further capsule housing (not shown) is intended to be coupled to the right-hand side of capsule housing part 310 to form an elongated ingestible capsule. Actuation member 350, taking the form of an elongated plunger or ram, is mounted for axial movement along an axis extending lengthwise through a cylindrical opening 315 of capsule housing part 310. The actuation member 350 is configured for sliding axial movement inside the cylindrical opening 315 from a pre-firing configuration which is shown (a proximal position), and in an axially distal direction into a fired configuration (not shown) where the plunger would have moved to the right in FIG. 6a (a distal position). In the pre-firing configuration, the compression spring 340 exerts a load onto the actuation member which urges the actuation member 350 distally towards the fired configuration. During release of the actuation mechanism, the device assumes a firing configuration which releases the actuation member for axial movement.

The distal end portion of the actuation member 350 forms a piston 355 which is received in close fitting relationship with the cylindrical opening 315 so that the piston is able to slide within cylindrical opening 315. From the piston 355 a reduced diameter shaft extends towards the proximal end of the actuation member 350. The proximal end of the reduced diameter shaft includes a recessed area which is configured for partly accommodating the latch member 352. Adjoining the recessed area, at the proximal end thereof, the shaft includes a first retainer portion 357. In the state shown in FIG. 6a, i.e. the pre-firing configuration, the dissolvable firing member or pellet 360 is arranged at the same axial location as the recessed area of the shaft.

In the shown embodiment, best viewed in FIG. 6b, the latch member 352 is formed as a generally elongated object extending transversely to the axis, the latch member being arranged so that only a part thereof is accommodated in the recessed area of the shaft. The latch member 352 includes a first blocking portion 353a and a second blocking portion 353b. A constriction is provided inside the cylindrical opening 315 at a position close to the most proximal end thereof. The constriction includes a recessed area wherein the dissolvable firing member 360 is received. An assembly of the capsule housing part 310 and the dissolvable firing member 360 forms a keyhole through which the shaft of the actuation member 350 protrudes while enabling no or only little lateral movement of the shaft inside the keyhole. The constriction forms a second retainer portion 313 inside the capsule housing 310, which as shown in FIG. 6a, i.e. the pre-firing configuration, is located distally from latch member 352 and dissolvable firing member 360. The second retainer portion 313 engages with the second blocking portion 353b of latch member 352 which serves to prevent the latch member 352 from moving distally relative to capsule housing part 310. In the shown embodiment, both the first blocking portion 353a and the first retainer portion 357 include mating inclined surfaces which lies in intimate contact with each other.

In the pre-firing configuration shown in FIGS. 6a and 6b, the dissolvable firing member 260 radially supports the latch member 352 at a surface 352a thereof. In this position the latch member 352 both engages the second retainer portion 313 as well as the first retainer portion 357. Hence, the latch member 352 prevents the actuation member 350 from moving distally. Upon the dissolvable firing member 360 becoming exposed to a fluid, such as stomach or intestinal fluid, the dissolvable firing member becomes at least partially dissolved inside the recessed area of the constriction. This enables lateral movement of the latch in a radial direction away the recessed area of the shaft of the actuation member 350 (i.e. upwards in FIG. 6a). The lateral movement is due to the drive spring 340 exerting a distally directed force on the actuation member 350, and due to the mating inclined surfaces of the first blocking portion 353a and the first retainer portion 357.

Upon sufficient dissolvement of the dissolvable firing member 360, the first retainer portion 357 of the shaft will be able to pass the first blocking portion 353a in which case the device assumes the firing configuration. This causes the drive spring 340 to expand freely until the actuation member 350 reaches the second position and the device sub-assembly 300 assumes the fired configuration.

Although the above description of exemplary embodiments mainly concern ingestible capsules for delivery in the stomach, the present actuation principle generally finds utility in capsule devices for lumen insertion in general, wherein a capsule device is positioned into a body lumen, and wherein a fluid activates an actuation mechanism by dissolving a dissolvable firing member for bringing a component from a first configuration into a second configuration, such as from a first position into a second position. Non-limiting examples of capsule devices may include capsule devices for intestinal delivery of a drug either by delivery into the intestinal lumen or into the tissue wall of an intestinal lumen. Drug delivery may be performed using a delivery member, such as a needle, or via micro-needles which is inserted into the tissue wall of a lumen, or which fires directly into the lumen. Alternatively, drug delivery may be performed through one or more exit openings of the capsule device without the use of a delivery member, such as by jet injection into a mucosal lining of a lumen wall.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical device suitable for insertion into a lumen of a patient, the lumen having a lumen wall, the medical device comprising:
   a capsule sized to be inserted into the lumen, the capsule comprising a base member, and
   an actuation mechanism comprising:
      an actuation member configured for movement relative to the base member along an axis, and
      an energy source associated with the actuation member for powering the actuation member to move relative to the base member along the axis,
   wherein the base member and the actuation member define a latch assembly comprising at least one pair of a latch and a retainer portion structured to maintain the actuation member in a pre-firing configuration, wherein for each pair of latch and retainer portion the medical device defines:
      a dissolvable firing member, the dissolvable firing member being at least partially dissolvable when subjected to a biological fluid,
      a retainer portion comprised by one of the base member and the actuation member, and
      a movable latch configured for lateral movement relative to the axis, the movable latch defining a first surface with a blocking portion, and a second surface configured for interacting with the dissolvable firing member,
   wherein the latch assembly is configured with an interface portion between the movable latch and the retainer portion,
   wherein the interface portion comprises an inclined surface portion that acts to transfer an axial load provided by the energy source, at least partly, into a lateral force urging the movable latch in a lateral direction,
   wherein in the pre-firing configuration, the blocking portion of the movable latch engages the retainer portion in a latching engagement, and the second surface of the movable latch interacts with the dissolvable firing member to restrict lateral movement of the movable latch thereby preventing release of the latching engagement, and
   wherein, in a firing configuration where the dissolvable firing member has become at least partially dissolved, the movable latch is allowed to move laterally thereby releasing the latching engagement between the blocking portion of the movable latch and the retainer portion to allow the energy source to fire the actuation member.

2. A medical device as in claim 1, wherein the latch assembly is structured so that the movable latch, in the pre-firing configuration, exclusively or primarily exerts a compression force, such as laterally directed force, upon the dissolvable firing member.

3. A medical device as in claim 1, wherein the second surface defines a support surface configured for interacting with the dissolvable firing member, wherein the second surface is disposed oppositely to the first surface.

4. A medical device as in claim 1, wherein the retainer portion is comprised by one of the base member and the actuation member, and wherein the movable latch is a deflectable latch comprised by the other of the base member and the actuation member, the deflectable latch being configured for lateral movement relative to the axis.

5. A medical device as in claim 1, wherein the movable latch is formed as an individual component arranged between the actuation member and the base member, and wherein the movable latch includes a third surface with a blocking portion, wherein the first surface with the blocking portion is configured to engage a retainer portion of one of the base member and the actuation member, and the third surface with the blocking portion is configured to engage a retainer portion of the other of the base member and the actuation member.

6. A medical device as in claim 1, wherein the dissolvable firing member is adjoined on two opposed surfaces by the movable latch on one of the two opposed surfaces and a load supporting surface on the other of the two opposed surfaces.

7. A medical device as in claim 1, wherein the blocking portion of the movable latch is formed as a right part of the actuation member, wherein the actuation mechanism is so configured that, in the firing configuration, a tilting movement of the actuation member is enabled relative to the axis, but wherein the dissolvable firing member in the pre-firing configuration prevents said tilting movement.

8. A medical device as in claim 1, wherein a plurality of pairs of latch and retainer portions, such as two, three, four, five or more pairs of latch and retainer portions are provided, the pairs of latch and retainer portions being disposed equally around the axis.

9. A medical device as in claim 1, wherein the dissolvable firing member is arranged along the axis, and wherein the at least one pair of latch and retainer portion is disposed radially outside of the dissolvable firing member.

10. A medical device as in claim 1, wherein the capsule comprises one or more openings to allow a biological fluid, such as gastric fluid to enter the capsule for dissolving the dissolvable firing member.

11. A medical device as in claim 1, wherein the medical device is configured as a drug delivery device for delivery of a solid drug, an encapsulated solid, a liquid, a gel or a powder, or any combination thereof.

12. A medical device as in claim 1, wherein the energy source is a spring, such as a compression spring, the spring being strained or configured for being strained for powering the actuation member.

13. A medical device as in claim 1, wherein the medical device defines an ingestible device suitable for swallowing by a patient and travelling into a lumen of a gastrointestinal tract of a patient.

14. A medical device as in claim 1, wherein the medical device is configured as a self-righting capsule, wherein when the self-righting capsule is at least partially supported by the tissue of the lumen wall, the self-righting capsule allows orienting in a pre-defined orientation prior to the medical device entering into the firing configuration.

15. A medical device suitable for insertion into a lumen of a patient, the lumen having a lumen wall, the medical device comprising:
 a capsule sized to be inserted into the lumen, the capsule comprising a base member, and
 an actuation mechanism comprising:
  an actuation member configured for movement relative to the base member along an axis, and
  an energy source associated with the actuation member for powering the actuation member to move relative to the base member along the axis,
wherein the base member and the actuation member define a latch assembly comprising at least one pair of a latch and a retainer portion structured to maintain the actuation member in a pre-firing configuration, wherein for each pair of latch and retainer portion the medical device defines:
 a dissolvable firing member, the dissolvable firing member being at least partially dissolvable when subjected to a biological fluid,
 a retainer portion comprised by one of the base member and the actuation member, and
 a movable latch configured for lateral movement relative to the axis, the movable latch defining a first surface with a blocking portion, and a second surface configured for interacting with the dissolvable firing member,
wherein the movable latch is formed as an individual component arranged between the actuation member and the base member, and wherein the movable latch includes a third surface with a blocking portion, wherein the first surface with the blocking portion is configured to engage a retainer portion of one of the base member and the actuation member, and the third surface with the blocking portion is configured to engage a retainer portion of the other of the base member and the actuation member,
wherein in the pre-firing configuration, the blocking portion of the movable latch engages the retainer portion in a latching engagement, and the second surface of the movable latch interacts with the dissolvable firing member to restrict lateral movement of the movable latch thereby preventing release of the latching engagement, and
wherein, in a firing configuration where the dissolvable firing member has become at least partially dissolved, the movable latch is allowed to move laterally thereby releasing the latching engagement between the blocking portion of the movable latch and the retainer portion to allow the energy source to fire the actuation member.

16. A medical device as in claim 15, wherein the latch assembly is structured so that the movable latch, in the pre-firing configuration, exclusively or primarily exerts a compression force, such as laterally directed force, upon the dissolvable firing member.

17. A medical device as in claim 15, wherein the second surface defines a support surface configured for interacting with the dissolvable firing member, wherein the second surface is disposed oppositely to the first surface.

18. A medical device as in claim 15, wherein the retainer portion is comprised by one of the base member and the actuation member, and wherein the movable latch is a deflectable latch comprised by the other of the base member and the actuation member, the deflectable latch being configured for lateral movement relative to the axis.

19. A medical device as in claim 15, wherein the dissolvable firing member is adjoined on two opposed surfaces by the movable latch on one of the two opposed surfaces and a load supporting surface on the other of the two opposed surfaces.

20. A medical device as in claim 15, wherein the blocking portion of the movable latch is formed as a right part of the actuation member, wherein the actuation mechanism is so configured that, in the firing configuration, a tilting movement of the actuation member is enabled relative to the axis, but wherein the dissolvable firing member in the pre-firing configuration prevents said tilting movement.

21. A medical device as in claim 15, wherein a plurality of pairs of latch and retainer portions, such as two, three, four, five or more pairs of latch and retainer portions are provided, the pairs of latch and retainer portions being disposed equally around the axis.

22. A medical device as in claim 15, wherein the dissolvable firing member is arranged along the axis, and wherein the at least one pair of latch and retainer portion is disposed radially outside of the dissolvable firing member.

23. A medical device as in claim 15, wherein the capsule comprises one or more openings to allow a biological fluid, such as gastric fluid to enter the capsule for dissolving the dissolvable firing member.

24. A medical device as in claim 15, wherein the medical device is configured as a drug delivery device for delivery of a solid drug, an encapsulated solid, a liquid, a gel or a powder, or any combination thereof.

25. A medical device as in claim 15, wherein the energy source is a spring, such as a compression spring, the spring being strained or configured for being strained for powering the actuation member.

26. A medical device as in claim 15, wherein the medical device defines an ingestible device suitable for swallowing by a patient and travelling into a lumen of a gastrointestinal tract of a patient.

27. A medical device as in claim 15, wherein the medical device is configured as a self-righting capsule, wherein when the self-righting capsule is at least partially supported by the tissue of the lumen wall, the self-righting capsule allows orienting in a pre-defined orientation prior to the medical device entering into the firing configuration.

28. A medical device suitable for insertion into a lumen of a patient, the lumen having a lumen wall, the medical device comprising:
a capsule sized to be inserted into the lumen, the capsule comprising a base member, and
an actuation mechanism comprising:
an actuation member configured for movement relative to the base member along an axis, and
an energy source associated with the actuation member for powering the actuation member to move relative to the base member along the axis,
wherein the base member and the actuation member define a latch assembly comprising at least one pair of a latch and a retainer portion structured to maintain the actuation member in a pre-firing configuration, wherein for each pair of latch and retainer portion the medical device defines:
a dissolvable firing member, the dissolvable firing member being at least partially dissolvable when subjected to a biological fluid,
a retainer portion comprised by one of the base member and the actuation member, and
a movable latch configured for lateral movement relative to the axis, the movable latch defining a first surface with a blocking portion, and a second surface configured for interacting with the dissolvable firing member,
wherein in the pre-firing configuration, the blocking portion of the movable latch engages the retainer portion in a latching engagement, and the second surface of the movable latch interacts with the dissolvable firing member to restrict lateral movement of the movable latch thereby preventing release of the latching engagement,
wherein, in a firing configuration where the dissolvable firing member has become at least partially dissolved, the movable latch is allowed to move laterally thereby releasing the latching engagement between the blocking portion of the movable latch and the retainer portion to allow the energy source to fire the actuation member, and
wherein the medical device is configured as a self-righting capsule, wherein when the self-righting capsule is at least partially supported by the tissue of the lumen wall, the self-righting capsule allows orienting in a pre-defined orientation prior to the medical device entering into the firing configuration.

29. A medical device as in claim 28, wherein the latch assembly is structured so that the movable latch, in the pre-firing configuration, exclusively or primarily exerts a compression force, such as laterally directed force, upon the dissolvable firing member.

30. A medical device as in claim 28, wherein the second surface defines a support surface configured for interacting with the dissolvable firing member, wherein the second surface is disposed oppositely to the first surface.

31. A medical device as in claim 28, wherein the retainer portion is comprised by one of the base member and the actuation member, and wherein the movable latch is a deflectable latch comprised by the other of the base member and the actuation member, the deflectable latch being configured for lateral movement relative to the axis.

32. A medical device as in claim 28, wherein the movable latch is formed as an individual component arranged between the actuation member and the base member, and wherein the movable latch includes, and a third surface with a blocking portion, wherein the first surface with the blocking portion is configured to engage a retainer portion of one of the base member and the actuation member, and the third surface with the blocking portion is configured to engage a retainer portion of the other of the base member and the actuation member.

33. A medical device as in claim 28, wherein the dissolvable firing member is adjoined on two opposed surfaces by the movable latch on one of the two opposed surfaces and a load supporting surface on the other of the two opposed surfaces.

34. A medical device as in claim 28, wherein the blocking portion of the movable latch is formed as a right part of the actuation member, wherein the actuation mechanism is so configured that, in the firing configuration, a tilting movement of the actuation member is enabled relative to the axis, but wherein the dissolvable firing member in the pre-firing configuration prevents said tilting movement.

35. A medical device as in claim 28, wherein a plurality of pairs of latch and retainer portions, such as two, three, four, five or more pairs of latch and retainer portions are provided, the pairs of latch and retainer portions being disposed equally around the axis.

36. A medical device as in claim 28, wherein the dissolvable firing member is arranged along the axis, and wherein the at least one pair of latch and retainer portion is disposed radially outside of the dissolvable firing member.

37. A medical device as in claim 28, wherein the capsule comprises one or more openings to allow a biological fluid, such as gastric fluid to enter the capsule for dissolving the dissolvable firing member.

38. A medical device as in claim 28, wherein the medical device is configured as a drug delivery device for delivery of a solid drug, an encapsulated solid, a liquid, a gel or a powder, or any combination thereof.

39. A medical device as in claim 28, wherein the energy source is a spring, such as a compression spring, the spring being strained or configured for being strained for powering the actuation member.

40. A medical device as in claim 28, wherein the medical device defines an ingestible device suitable for swallowing by a patient and travelling into a lumen of a gastrointestinal tract of a patient.

* * * * *